United States Patent [19]

Morgan et al.

[11] Patent Number: 4,503,849
[45] Date of Patent: Mar. 12, 1985

[54] ARM RESTRAINT FOR BLOOD SAMPLING

[76] Inventors: William E. Morgan; Patsy A. Morgan, both of 12012 Ringwood, Norwalk, Calif. 90650

[21] Appl. No.: 418,730

[22] Filed: Sep. 16, 1982

[51] Int. Cl.³ .............................................. A61M 5/00
[52] U.S. Cl. .................................. 128/133; 128/89 R; 128/DIG. 6
[58] Field of Search ................. 128/133, 134, 132, 87, 128/89, DIG. 6

[56] References Cited

U.S. PATENT DOCUMENTS

| | | | |
|---|---|---|---|
| 2,266,230 | 12/1941 | Mazzeo et al. | 128/DIG. 26 |
| 2,266,231 | 12/1941 | Mazzeo et al. | 128/DIG. 26 |
| 2,693,794 | 11/1954 | Neville | 128/133 X |
| 3,256,880 | 6/1966 | Caypinar | 128/133 |
| 3,480,013 | 5/1967 | Garber | |
| 3,640,273 | 2/1972 | Ray | 128/133 |
| 3,724,456 | 4/1973 | Waxman | |
| 3,776,255 | 12/1973 | Lonardo | 128/77 |
| 3,812,851 | 5/1974 | Rodriguez | 128/133 |
| 4,043,330 | 8/1977 | Bansal | 248/118 |

FOREIGN PATENT DOCUMENTS 1171345 11/1969 United Kingdom ............... 128/133

Primary Examiner—Stephen C. Pellegrino
Attorney, Agent, or Firm—Howard A. Kenyon

[57] ABSTRACT

An arm restraint for temporarily restraining a patient's arm while drawing either venous or arterial blood is described. The restraint includes a rigid member with a concave cross section to accept an arm from the upper part of the arm to below the wrist. Adjustable and removable straps are at each end of the rigid member with securing straps attached through slots in the rigid member substantially in the middle of the rigid member. The securing straps can be used to attach the arm restraint to a bed rail, a blood collecting chair or the like. Spring clips are attached to the underside of the rigid member to attach a blood collecting tray. An open ended slot is available at one end of the rigid member through which a tourniquet passes and continues around the patient's upper arm.

6 Claims, 5 Drawing Figures

ARM RESTRAINT FOR BLOOD SAMPLING

BACKGROUND OF THE INVENTION

1. Field of the Invention

This invention relates to a device to assist in blood sampling or drawing blood from a patient's arm.

2. Description of the Prior Art

The prior art has provided a variety of devices to restrain a patient's arm for use by doctors and hospitals. Typical devices are temporary arm splints for holding a broken arm in place. Other arm restraints which are commercially available are used for intravenous feeding, however, most hospitals presently use a padded styrofoam board or the like for intravenous feeding and simply dispose of the padded board when it is no longer needed by the patient. A number of non-disposable arm boards for intravenous feeding are disclosed in the prior art. One such device is disclosed in U.S. Pat. No. 4,043,330 to Bansal which issued in 1977.

Another type of restraining device disclosed for intravenous feeding is U.S. Pat. No. 3,256,880 to Caypinac issued in 1966.

Still another device is U.S. Pat. No. 3,776,225 to Lonardo who disclosed an arm splint which may be used for intravenous feedings. Additionally, U.S. Pat. No. 3,724,456 to Waxman disclosed an extremity support for intravenous feeding. All of these devices, however, have as their primary object, means for intravenous feeding. It is well known that an intravenous feeding device is a long term restraining device that will maintain the arm immobile. It is also well known that intravenous feeding is an extremely slow and time consuming process and therefore the object of most of the devices described herein is to maintain a patient's arm immobilized during intravenous treatment with the least amount of discomfort and trauma to the patient. However, a visit to any acute hospital will reveal that none of the prior art has had any commercial success.

In the present invention the arm restraint is developed specifically for blood drawing and/or blood sampling and is not intended to be used for a long term intravenous feeding device. The parts of the arm restraint are designed to be quickly attached and adjusted and the arm restraint will find its greatest use when a delirious patient, an uncooperative patient or a uncooperative child must have blood drawn quickly for typing and the like. The present invention will also find use in today's hospitals where at times during a 24 hours shift a specialist must work all alone with a patient who is critically ill yet will not cooperate in the drawing of blood. Due to the unique design of the present invention, either venous or arterial blood may be drawn quickly and safely from the patient's arm.

SUMMARY OF THE INVENTION

It is the object of the invention to provide a portable arm restraint for blood sampling.

It is another object of this invention to provide a portable rigid member to restrain an arm during blood sampling.

It is a further object of this invention to provide a portable rigid member with quickly adjustable straps to hold a patient's arm secure to the rigid member to restrain the arm while drawing blood.

It is yet another object of this invention to provide quickly adjustable straps to strap the rigid member to a bed rail or blood collecting chair while drawing blood.

Briefly, in accordance with this invention, there is provided a portable arm restraint for collecting blood designed to be quickly attached to the patient's arm and also quickly removed from the patient's arm. The arm restraint has a rigid, concave member extending from the patient's upper arm to below the patient's wrist. The rigid member curves up in the area of the elbow and curves down in the area of the wrist to gently bend the wrist backward. This allows venous blood to be drawn from the vein opposite the elbow bone and arterial blood to be drawn from the arteries in the front of the wrist. The rigid member contains snaps to attach the straps to the patient's upper arm and wrist and slots approximately mid-point to attach a strap to a bed rail, chair or the like. The rigid member also contains clips on the back side to hold a blood collecting tray.

The novel features which are believed to be characteristics of the invention, both as to its organization and its method of operation, together with further objects and advantages thereof, will be better understood from the following description in connection with the accompanying drawings in which a presently preferred embodiment of the invention is illustrated by way of example. It is to be expressly understood, however, that the drawings are for purposes of illustration and description only, and are not intended as a definition of the limits of the invention.

While the invention will be described in connection with the preferred embodiment, it will be understood that it is not intended to limit the invention to that embodiment. On the contrary, it is intended to cover all alternatives, modifications, and equivalents that may be included within the spirit and scope of the invention as defined by the appended claims.

DETAILED DESCRIPTION OF THE INVENTION

Figure 1:
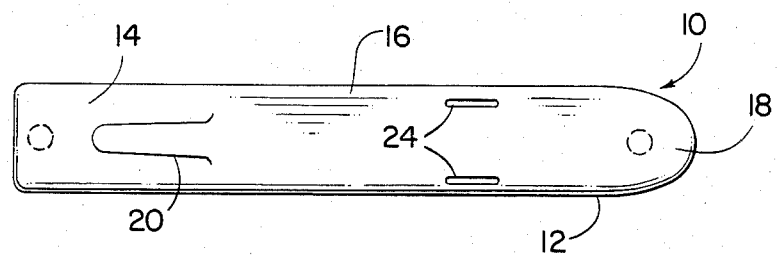
FIG. 1 is a top view of the arm restraint for blood sampling.

Referring now to FIG. 1, there is shown an arm restraint for temporarily restraining a patient's arm while drawing blood, generally indicated at 10. The rigid member 12 can be manufactured from plastic, fiberglass, light weight metal or some other suitable material that can be manufactured easily and at a low cost. Rigid member 12 must also be capable of withstanding sterilization temperatures (i.e., 212° for approximately 10 minutes) which are reached in medical sterilization equipment without damage. Rigid member 12 is also a concave shape and is designed such that the back of the patient's upper arm (not shown) will fit into area 14. Rigid member 12 is also designed such that the patient's forearm (not shown) will fit into the area 16 and the back of the patient's wrist (not shown) will fit into the area 18. Tang 20 is spaced above rigid body area 14 such that slot (22 in FIG. 2) is available to accept a tourniquet (not shown) which is further wrapped around a patient's upper arm. The tourniquet restricts the flow of venous blood in the patient's upper arm which in turn makes the veins in the area of the elbow protrude and allows the specialist better access when drawing venous blood. Slots 24 are designed to accept a strap that is used to secure the arm restraint to a bed rail, blood collecting chair or the like.

Figure 2:
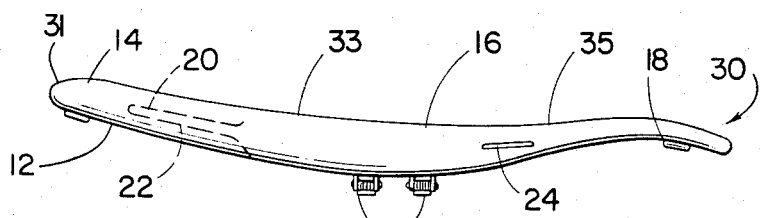
FIG. 2 is a side view of the arm restraint for blood sampling.
Figure 4:
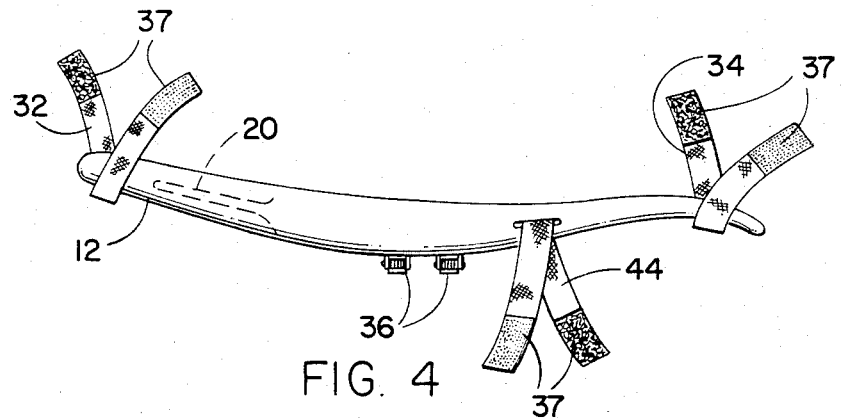
FIG. 4 is a view similar to FIG. 2 showing the placement of the straps.

Referring now to FIG. 2 which is a side view of the arm restraint, generally indicated at 30, there is shown the slope of the rigid member 12 which starts at the point 31 with a gentle slope to point 33, then a gentle slope to point 35 whereby rigid member 12 slopes sharply down to engage the back of the wrist. The slope of the rigid member from point 31 to point 33 and thereafter to point 35 is necessary to immobolize the elbow area in order to be able to more readily puncture a venous blood vessel. The slope of the rigid member 12 curves downward from point 35 whereby the back or the wrist will fit and be secured by straps 34 (FIG. 4). This gives an excellent position to draw arterial blood since the wrist area on the same side as the patient's palm is usually the area where arterial blood is drawn. Straps 32 (FIG. 4) will hold the upper arm securely in the concave rigid member 12. Spring clips 36 are designed to hold a blood collecting tray and are attached by fastening means to the bottom of rigid member 12.

Figure 3:
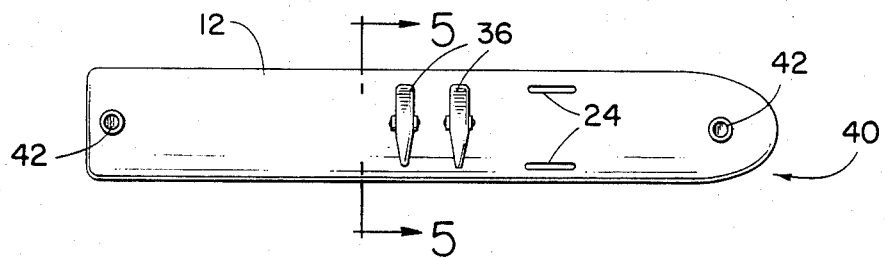
FIG. 3 is a bottom view of the arm restraint for blood sampling.

Referring to FIG. 3 which is a bottom view of the arm restraint, generally indicated at 40, there are shown clips 36 and slots 24 designed into rigid member 12. Also shown are snaps 42 whereby straps 32 and 34 snap onto rigid member 12. This is designed such that straps 32 and 34 may be easily removed for cleaning and sterilization.

Referring to FIG. 4, in addition to straps 32 and 34 described above, there is also shown straps 44 that are used to secure rigid member 12 to a bed rail or blood collecting chair. To provide a quick adjustment, all of the inside of the ends of straps 32, 34 and 44 are provided with a prickly surface 32 to obtain an interlock such as that obtained by Velcro, made by the Velcro Corp.

Figure 5:
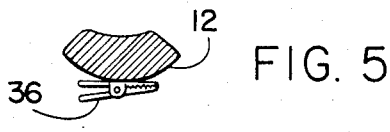
FIG. 5 is a cross section of FIG. 3 also showing the clips that can be used to hold a blood collecting tray.

FIG. 5 shows a cross section of rigid member 12 defining how rigid member 12 is a concave shape to hold the patient's arm secure. A side view of the spring clips designed to hold a blood collecting tray is also shown.

FIGS. 1, 2, 3 and 4 describe a non-dimensional arm restraint. It is obvious that one universal size will not fit all patients, therefore, arm restraint as described herein will be manufactured in 3 sizes to fit and adult, an adolescent and a child. This size division is necessary if the arm restraint is to serve its intended purpose, especially in emergency and critical situations.

Defining the operation of the preferred embodiment of the arm restraint for blood sampling as described in FIGS. 1, 2, 3 and 4, the patient would most likely be in the prone position, preferably lying on his back. With the present invention, the blood drawing operation is easily accomplished whether the patient is unconscious or conscious. The rigid member 12 is placed on the back of the patient's arm. The area 18 will fit on the back of the patient's wrist and the area 16 will fit on the back of the patient's forearm. The back of the patient's upper arm will thereby fit on the area described by 14. Straps 32 and 34 are secured about the patient's upper arm and wrist respectively and secured by a velcro fastener. If required, straps 44 can be used to secure the arm restraint device to a bed rail or the like. With the arm completely immobolized, the technician, nurse or physician is now ready to draw either venus blood or arterial blood, whichever is required. A blood collecting tray may be fastened to spring clips 36 if desired to hold instruments, gauze, tape and the like.

It will be readily apparent to those skilled in the art that various modifications and changes can be made without departing from the spirit of the invention.

Thus, it is apparent that there has been provided in accordance with the invention, an arm restraint for temporarily restraining a patient's arm while drawing blood that fully satisfies the objectives, aims and advantages set forth above. While the invention has been described in conjunction with the specific embodiments thereof, it is evident that many alternatives, modifications, and variations will be apparent to those skilled in the art in light of the aforegoing description. Accordingly, it is intended to embrace all such alternatives, modifications, and variations that fall within the spirit and scope of the appended claims.

What is claimed is:

1. An arm restraint for immobilizing the arm of a patient while drawing blood comprising:
   a rigid member having an upper, middle and lower portion;
   a curved upper arm rigid member having a cross section shape designed to fit the back of a patient's upper arm and further comprising tourniquet attaching means in said upper arm rigid member and a snap on the backside of the end of said upper arm rigid member;
   a middle arm rigid member having a concave cross section shape designed to fit a patient's elbow area and the back of a patient's forearm and further containing slots on each side of said middle arm rigid member with a first holding strap fitted therethrough and further comprising means for attaching a tray to the back of said concave shape of said middle arm rigid member, and
   a lower arm rigid member having a reverse curve from said upper arm rigid member and further having a concave cross section shape designed to fit a patient's wrist area and further containing a snap on the backside of the end of said lower arm rigid member.

2. An arm restraint as described in claim 1 wherein said tourniquet attaching means is a tang located in the bottom of said concave portion of said upper arm rigid member.

3. An arm restraint as described in claim 1 wherein said means for attaching a tray to the back of said concave shape of said middle arm rigid member are spring clips.

4. An arm restraint as described in claim 1 wherein said first holding strap is fastened to a gurney rail, a bed rail or the like.

5. An arm restraint as described in claim 1 wherein said snap of the backside of the end of said upper arm rigid member fits a snap for holding said upper arm rigid member firmly to said patient's upper arm.

6. An arm restraint as described in claim 1 wherein said snaps on the backside of the end of said lower arm rigid member fits a snap fastened to the middle of a third holding strap for holding said lower arm rigid member firmly to said patient's wrist area.

* * * * *